(12) United States Patent
Hayashibara et al.

(10) Patent No.: US 6,500,978 B2
(45) Date of Patent: Dec. 31, 2002

(54) PROCESS FOR PRODUCING CYCLOPROPANECARBONITRILE

(75) Inventors: Tatsuhiko Hayashibara, Kitakanbara (JP); Junko Sato, Kitakanbara (JP); Eriko Matsuda, Kitakanbara (JP); Masahiro Torihara, Kitakanbara (JP); Yoshin Tamai, Kitakanbara (JP)

(73) Assignee: Kuraray Co., Ltd., Kurashiki (JP)

(*) Notice: Subject to any disclaimer, the term of this patent is extended or adjusted under 35 U.S.C. 154(b) by 0 days.

(21) Appl. No.: 10/081,231

(22) Filed: Feb. 25, 2002

(65) Prior Publication Data

US 2002/0120163 A1 Aug. 29, 2002

(30) Foreign Application Priority Data

Feb. 23, 2001 (JP) .................................. 2001-048030
Sep. 11, 2001 (JP) .................................. 2001-275152

(51) Int. Cl.$^7$ ............................................ C07C 255/00
(52) U.S. Cl. ...................................................... 558/434
(58) Field of Search ........................................ 558/434

(56) References Cited

U.S. PATENT DOCUMENTS

| | | |
|---|---|---|
| 3,853,942 A | 12/1974 | Sury et al. |
| 5,362,911 A | 11/1994 | Cevasco |
| 5,380,911 A | 1/1995 | Strong |
| 5,405,998 A | 4/1995 | Cevasco |
| 5,502,234 A | 3/1996 | Liang |
| 5,977,414 A | 11/1999 | Okabe et al. |

FOREIGN PATENT DOCUMENTS

| | | |
|---|---|---|
| DE | 3303704 A1 | 8/1984 |
| DE | 3639 158 A1 | 5/1988 |
| DE | 269 149 A1 | 6/1989 |
| JP | 7-188132 | 7/1995 |
| NL | 7713925 | 6/1979 |

*Primary Examiner*—T. A. Solola
*Assistant Examiner*—Joseph Murray
(74) *Attorney, Agent, or Firm*—Oblon, Spivak, McClelland, Maier & Neustadt, P.C.

(57) ABSTRACT

A process for producing cyclopropanecarbonitrile involves reacting cyclopropanecarbaldoxime with acetic anhydride to obtain a mixture containing acetic acid and cyclopropanecarbonitrile. The acetic acid can be removed from the mixture through azeotropic distillation of acetic acid with a solvent that forms with acetic acid an azeotropic mixture having an azeotropic point lower than the boiling point of the cyclopropanecarbonitrile.

20 Claims, No Drawings

PROCESS FOR PRODUCING CYCLOPROPANECARBONITRILE

BACKGROUND OF THE INVENTION

1. Field of the Invention

The present invention relates to a process for producing cyclopropanecarbonitrile.

2. Discussion of the Background

Cyclopropanecarbonitrile is useful as a material for producing aminophenylketones, which in turn can be used to produce sulfamoylurea herbicides, which are well-known herbicides applied to paddy-rice plants (See, Japanese Patent Laid-Open Publication No. Hei 7-188132 (188132/1995)).

Conventional processes for producing cyclopropanecarbonitrile include (1) a process as described in U.S. Pat. No. 3,853,942 and U.S. Pat. No. 5,380,911 that involves intramolecular cyclization of halobutyronitrile using a base, and (2) a process as described in U.S. Pat. No. 5,502,234 that involves converting cyclopropanecarbaldehyde into cyclopropanecarbaldoxime, which in turn is dehydrated using formic acid to form cyclopropanecarbonitrile, and neutralizing the resulting reaction mixture with an alkali metal compound.

However, the process (1) has a disadvantage that synthesis of halobutyronitrile, such as 4-chlorobutyronitrile, requires the use of expensive bromochloropropane, and nitrilization of bromochloropropane requires the use of toxic cyanogen compounds. On the other hand, in the process (2), the reaction mixture needs to be neutralized, following the dehydration, with an alkali metal compound and leads to the problem of the disposition of waste water containing alkali metal salt of formic acid as by-product formed in the process in abundance.

SUMMARY OF THE INVENTION

Accordingly, it is an object of the present invention to provide a process for producing cyclopropanecarbonitrile that can produce cyclopropanecarbonitrile in good yields in a safe, economical, and industrially advantageous manner.

In one aspect, the present invention provides a process for producing cyclopropanecarbonitrile, which is characterized in that cyclopropanecarbaldoxime is reacted with acetic anhydride.

In another aspect, the present invention provides a process for producing cyclopropanecarbonitrile that involves reacting cyclopropanecarbaldoxime with acetic anhydride to obtain a mixture containing acetic acid and cyclopropanecarbonitrile, and removing acetic acid from the mixture through azeotropic distillation of acetic acid with a solvent that forms with acetic acid an azeotropic mixture having an azeotropic point lower than the boiling point of the cyclopropanecarbonitrile.

In a preferred embodiment of the present invention, the above-mentioned removal of acetic acid through azeotropic distillation is achieved by using a hydrocarbon that forms with acetic acid an azeotropic mixture having an azeotropic point lower than the boiling point of the cyclopropanecarbonitrile.

DETAILED DESCRIPTION OF PREFERRED EMBODIMENTS

Cyclopropanecarbaldoxime for use in the present invention can be readily produced by, for example, reacting cyclopropanecarbaldehyde with hydroxylamine. In the present invention, cyclopropanecarbaldoxime produced through the above-mentioned process may be used in the form of either a reaction mixture without purification or a purified product. When cyclopropanecarbaldoxime is to be used in the form of a reaction mixture, it is preferred to remove water from the reaction mixture through azeotropic distillation of water using a solvent, such as toluene, that forms an azeotropic mixture with water, in order to increase the reaction rate. Cyclopropanecarbaldoxime has two isomers, namely, a cis-form and a transform, which may be used independently or as a mixture of the two in the present invention.

The molar amount of acetic anhydride used in the present invention is preferably from 0.5 to 20 times, more preferably from 1 to 5 times, as much as that of cyclopropanecarbaldoxime.

The reaction of the present invention may be carried out in the presence or in the absence of a solvent. Examples of the solvent include aliphatic or aromatic hydrocarbon solvents such as hexane, heptane, octane, 2,5-dimethylhexane, cyclohexane, methylcyclohexane, toluene, xylene, ethylbenzene, styrene and cumene; halogenated hydrocarbon solvents such as chlorobenzene, 1,2-dichloropropane, 1,2-dibromopropane, butyl bromide, 1-bromo-3-methylbutane, propyl iodide and isobutyl iodide; ether solvents such as diethyl ether, isopropyl ether, t-butyl methyl ether and 1,4-dioxane; nitroethane and 1-butanol. Of these, the aliphatic or aromatic hydrocarbon solvents such as hexane, heptane, octane, toluene, xylene, ethylbenzene and cumene are preferred. The amount in mass of the solvent, if used, is preferably 50 times as much as that of cyclopropanecarbaldoxime or less, and more preferably from 1 to 10 times as much as that of cyclopropanecarbaldoxime. The reaction may be carried out either in a solution or in a slurry.

The reaction is preferably carried out at a temperature of 50 to 120° C., more preferably 80 to 110° C., in consideration of the reaction rate and selectivity. Preferably, the reaction time is from about 3 to about 20 hours.

While cyclopropanecarbonitrile can be isolated from the resulting reaction mixture by simply distilling the reaction mixture, but it is preferred in one embodiment of the present invention that a solvent that forms with acetic acid an azeotropic mixture having an azeotropic point lower than the boiling point of cyclopropanecarbonitrile is added to the above-mentioned reaction mixture and the resulting mixture is distilled to remove acetic acid based on the principle of azeotropic distillation first. Subsequently the remaining mixture is distilled to obtain cyclopropanecarbonitrile. Examples of the solvent that forms with acetic acid an azeotropic mixture having an azeotropic point lower than the boiling point of cyclopropanecarbonitrile include aliphatic or aromatic hydrocarbon solvents such as hexane, heptane, octane, 2,5-dimethylhexane, cyclohexane, methylcyclohexane, toluene, xylene, ethylbenzene, styrene and cumene; halogenated hydrocarbon solvents such as chlorobenzene, 1,2-dichloropropane, 1,2-dibromopropane, butyl bromide, 1-bromo-3-methylbutane, propyl iodide and isobutyl iodide; 1,4-dioxane; nitroethane and 1-butanol. Of these, the aliphatic or aromatic hydrocarbon solvents such as hexane, heptane, octane, toluene, xylene, ethylbenzene and cumene are particularly preferred in consideration of effects on environment and safety.

When the reaction of cyclopropanecarbaldoxime with acetic anhydride is carried out in the presence of the above-mentioned solvent, the generated acetic acid can be removed by taking advantage of the principle of azeotropic distillation as the reaction progresses.

While the removal of acetic acid based on azeotropic distillation can be carried out under normal pressure, if necessary, it may be carried out under reduced pressure. In such a case, the temperature of the system may vary depending on the pressure, but it is preferably maintained in the range of 40 to 120° C., more preferably in the range of 80 to 110° C.

After the removal of acetic acid, cyclopropanecarbonitrile can be isolated and/or purified from the reaction mixture remaining by using a common technique for isolating and/or purifying an organic compound, for example, distillation under reduced pressure. The purity of cyclopropanecarbonitrile can be readily increased in this manner.

According to the present invention, cyclopropanecarbonitrile can be produced in good yields, in a safe, economical, and industrially advantageous manner.

EXAMPLES

The present invention will now be described in detail below, but it should however be borne in mind that the present invention is not limited to or by the following examples.

Reference Example 1

Synthesis of Cyclopropanecarbaldoxime

Cyclopropanecarbaldehyde (70.1 g (1.0 mol)) was placed in a 500 ml volume four-necked flask, equipped with a stirrer, a dropping funnel and a thermometer. Hydroxylamine (68.1 g; a 50 weight % aqueous solution (1.0 mol)) was then added dropwise over 3 hours while stirring the reaction mixture and maintaining the temperature thereof at 40° C. or lower. Subsequent to the addition of the hydroxylamine solution, the reaction mixture was stirred for 3 hours at room temperature. When cyclopropanecarbaldoxime crystallized from the reaction mixture, 1.5 L of isopropyl ether was added to the reaction mixture to dissolve the crystals. An organic layer and an aqueous layer were then separated. The organic layer was concentrated under reduced pressure to obtain 80.5 g (0.945 mol, 94.5% yield) of crystallized cyclopropanecarbaldoxime.

EXAMPLE 1

Cyclopropanecarbaldoxime (4.25 g (50 mmol)) obtained through the process of Reference Example 1 and toluene (20 ml) were placed in a 50 ml volume three-necked flask equipped with a stirrer, a dropping funnel and a thermometer. To this solution, acetic anhydride (5.6 g (55 mmol)) was added dropwise over 5 minutes. The resulting reaction mixture was heated to 105 to 110° C. and stirred for 9 hours. The results of gas chromatography analysis of the reaction mixture indicated that 3.18 g (47.5 mol) of cyclopropanecarbonitrile was contained (95% yield).

EXAMPLE 2

Cyclopropanecarbaldehyde (140 g (2.0 mol)) and toluene (140 ml) were placed in a 500 ml volume four-necked flask equipped with a stirrer, a dropping funnel and a thermometer. To this solution, hydroxylamine (136.2 g; a 50 weight% aqueous solution (2.05 mol)) was added dropwise over one and a half hours while stirring the reaction mixture and maintaining the temperature thereof in a range of 20 to 25° C. Subsequent to the addition of the hydroxylamine solution, the reaction mixture was heated to 40° C. and stirred for 2 hours. An organic layer and an aqueous layer were then separated. The aqueous layer was then extracted with toluene (40 g) and the extract was combined to the above separated organic layer. The mixture was then transferred to a 1L volume four-necked flask equipped with a stirrer, a dropping funnel and a thermometer. After the mixture was heated to 60° C., 224. 6 g (2.20 mol) of acetic anhydride was then added dropwise over 50 minutes. Subsequent to the addition of acetic anhydride, the reaction mixture was continuously heated for 7 hours at 105 to 110° C. Further acetic anhydride (22.5 g (0.22 mol)) was added to the reaction mixture, and heating was continued in the same temperature range for additional 8 hours. The results of gas chromatography analysis of 580.5 g of the resulting reaction mixture indicated that 125.4 g (1.87 mol) of cyclopropanecarbonitrile was contained (93.5% yield based on cyclopropanecarbaldehyde).

Reference Example 2

Synthesis of Cyclopropanecarbaldoxime

Hydroxylamine sulfate (41.6 g (0.25 mol)) and water (128 g) were placed in a 500 ml volume four-necked flask equipped with a stirrer, a dropping funnel and a thermometer. To the mixture was added sodium hydroxide (20.9 g (0.50 mol)) and neutralized. After stirring the mixture for 30 minutes at room temperature, toluene (35 g) was added, and then cyclopropanecarbaldehyde (35.05 g (0.50 mol)) was added dropwise over 15 minutes. Subsequent to the addition of cyclopropanecarbaldehyde, the reaction mixture was stirred for 3 hours at room temperature and was heated to 50° C. An organic layer and an aqueous layer were separated. The results of gas chromatography analysis of the organic layer indicated that 39.53 g (0.46 mol) of cyclopropanecarbaldoxime was contained (92.9% yield). Also, 2.97 g (0.035 mol) of cyclopropanecarbaldoxime was contained in the aqueous layer (equivalent to 7% yield) determined by gas chromatography analysis. Subsequently, water was removed together with toluene from the said organic layer through azeotropic distillation to obtain a 69.8 g (52.4 weight % of toluene solution) of cyclopropanecarbaldoxime.

EXAMPLE 3

The 69.8 g (52.4 weight % of toluene solution (0.43 mol)) of cyclopropanecarbaldoxime obtained through the process of Reference Example 2 was placed in a 500 ml volume four-necked flask equipped with a stirrer, a dropping funnel, a thermometer and a reflux condenser and was heated to 55° C. To the solution, 46.2 g (0.45 mol) of acetic anhydride was added dropwise over 36 minutes, and the mixture was stirred for 5 hours at 105 to 110° C. The results of gas chromatography analysis of the resulting reaction mixture indicated that 27.53 g (0.41 mol) of cyclopropanecarbonitrile was contained (95.4% yield).

EXAMPLE 4

247.8 g of a reaction mixture (containing 57.5 g of cyclopropanecarbonitrile) obtained through the same process as in Example 3 was placed in a 500 ml volume four-necked flask equipped with a stirrer, a 50 ml dropping funnel, a thermometer and a distillation tower (2.4 cm diameter×26 cm length) packed with helipack. Maintaining the temperature of the reaction mixture at 101° C. or lower, with portions of toluene added as necessary, acetic acid was removed together with toluene from the reaction mixture through azeotropic distillation under reduced pressure. The total amount of the portions of toluene added was 280 g. The resulting residue was distilled under reduced pressure to obtain 42.6 g (0.62 mol) of cyclopropanecarbonitrile having a purity of 99% or higher (72% yield after distillation) as determined by gas chromatography analysis.

While the present invention has been described with respect to specific embodiments, it is not confined to the specific details set forth, but includes various changes and modifications that may suggest themselves to those skilled in the art, all falling within the scope of the invention as defined by the following claims.

The disclosures of the priority documents, Japanese Patent Application No. 48030/2001, filed Feb. 23, 2001, and Japanese Patent Application No. 275152/2001, filed Sep. 11, 2001, are incorporated by reference herein in their entireties.

What is claimed is:

1. A process for producing cyclopropanecarbonitrile, the process comprising reacting cyclopropanecarbaldoxime with acetic anhydride.

2. The process according to claim 1, wherein the cyclopropanecarbaldoxime is ciscyclopropanecarbaldoxime.

3. The process according to claim 1, wherein the cyclopropanecarbaldoxime is trans-cyclopropanecarbaldoxime.

4. The process according to claim 1, wherein a molar ratio of the acetic anhydride to the cyclopropanecarbaldoxime is in a range of from 0.5 to 20.

5. The process according to claim 1, wherein the cyclopropanecarbaldoxime is reacted with the acetic anhydride in the presence of a solvent comprising at least one of an aliphatic or aromatic hydrocarbon solvent; a halogenated hydrocarbon solvent; an ether solvent; nitroethane and 1-butanol.

6. The process according to claim 5, wherein the aliphatic or aromatic hydrocarbon solvent is selected from the group consisting of hexane, heptane, octane, 2,5-dimethylhexane, cyclohexane, methylcyclohexane, toluene, xylene, ethylbenzene, styrene and cumene.

7. The process according to claim 5, wherein the halogenated hydrocarbon solvent is selected from the group consisting of chlorobenzene, 1,2-dichloropropane, 1,2 -dibromopropane, butyl bromide, 1-bromo-3-methylbutane, propyl iodide and isobutyl iodide.

8. The process according to claim 5, wherein the ether solvent is selected from the group consisting of diethyl ether, isopropyl ether, t-butyl methyl ether and 1,4-dioxane.

9. The process according to claim 1, wherein the cyclopropanecarbaldoxime and the acetic anhydride are reacted at a temperature in a range of from 50 to 120° C.

10. The process according to claim 1, wherein the cyclopropanecarbaldoxime and the acetic anhydride are reacted at a temperature in a range of from 80 to 110° C. for a period of time ranging of from 3 to 20 hours.

11. A process for producing cyclopropanecarbonitrile, the process comprising reacting cyclopropanecarbaldoxime with acetic anhydride to obtain a mixture containing acetic acid and cyclopropanecarbonitrile; and removing at least a portion of the acetic acid from the mixture through azeotropic distillation of the acetic acid with a solvent that forms with the acetic acid an azeotropic mixture having an azeotropic point lower than the boiling point of the cyclopropanecarbonitrile.

12. The process according to claim 1, wherein the solvent comprises at least one of an aliphatic or aromatic hydrocarbon solvent; a halogenated hydrocarbon solvent; 1,4-dioxane; nitroethane and 1-butanol.

13. The process according to claim 12, wherein the solvent comprises the aliphatic or aromatic hydrocarbon solvent.

14. The process according to claim 13, wherein the aliphatic or aromatic hydrocarbon solvent is selected from the group consisting of hexane, heptane, octane, 2,5-dimethylhexane, cyclohexane, methylcyclohexane, toluene, xylene, ethylbenzene, styrene and cumene.

15. The process according to claim 12, wherein the halogenated hydrocarbon solvent is selected from the group consisting of chlorobenzene, 1,2-dichloropropane, 1,2-dibromopropane, butyl bromide, 1-bromo-3-methylbutane, propyl iodide and isobutyl iodide.

16. The process according to claim 11, wherein the azeotropic distillation is carried out at atmospheric pressure.

17. The process according to claim 11, wherein the azeotropic distillation is carried out at a pressure below atmospheric pressure.

18. The process according to claim 17, wherein the azeotropic distillation is carried out at a temperature in a range of from 40 to 120° C.

19. The process according to claim 11, wherein the at least a portion of the acetic acid is removed from the mixture through the azeotropic distillation while the cyclopropanecarbaldoxime reacts with the acetic anhydride.

20. The process according to claim 11, further comprising distilling the cyclopropanecarbonitrile from the mixture at a pressure below atmospheric pressure.

* * * * *